United States Patent
Sentosa et al.

(10) Patent No.: US 10,062,259 B2
(45) Date of Patent: Aug. 28, 2018

(54) POOL FLOATATION DEVICE WITH SONAR

(71) Applicant: Superior Communications, Inc., Irwindale, CA (US)

(72) Inventors: Samuel Sentosa, Rancho Cucamonga, CA (US); George Chen, Chatsworth, CA (US); Adam Cho, Brea, CA (US)

(73) Assignee: SUPERIOR COMMUNICATIONS, INC., Irwindale, CA (US)

( * ) Notice: Subject to any disclaimer, the term of this patent is extended or adjusted under 35 U.S.C. 154(b) by 0 days.

(21) Appl. No.: 15/282,427

(22) Filed: Sep. 30, 2016

(65) Prior Publication Data

US 2017/0098361 A1    Apr. 6, 2017

Related U.S. Application Data (60) Provisional application No. 62/236,015, filed on Oct. 1, 2015.

(51) Int. Cl.
*G08B 21/08* (2006.01)
*G01N 33/18* (2006.01)
*B63B 22/00* (2006.01)

(52) U.S. Cl.
CPC ............ *G08B 21/08* (2013.01); *G01N 33/18* (2013.01); *B63B 2022/006* (2013.01)

(58) Field of Classification Search
CPC .. B63B 2035/006; B63B 35/00; G01N 33/18; G08B 21/08
USPC ........................................................ 367/93
See application file for complete search history.

(56) References Cited

U.S. PATENT DOCUMENTS

| | | | | |
|---|---|---|---|---|
| 7,510,651 | B1* | 3/2009 | Auger | C02F 1/688 210/167.11 |
| 8,134,462 | B1* | 3/2012 | Tran | G08B 21/084 340/10.1 |
| 2003/0222782 | A1* | 12/2003 | Gaudreau | G08B 21/082 340/573.6 |
| 2006/0292043 | A1* | 12/2006 | Biberger | G01N 33/18 73/53.01 |
| 2008/0106422 | A1* | 5/2008 | Sparks | E04H 4/14 340/573.6 |
| 2014/0268678 | A1* | 9/2014 | Potucek | F21V 23/0471 362/101 |
| 2014/0366612 | A1* | 12/2014 | Horne | G01F 1/66 73/40.5 A |
| 2015/0161870 | A1* | 6/2015 | Podlisker | G08B 21/08 340/573.6 |
| 2016/0091431 | A1* | 3/2016 | Clark | A61K 36/185 436/150 |
| 2016/0104359 | A1* | 4/2016 | AlMahmoud | G08B 21/08 367/112 |

(Continued)

FOREIGN PATENT DOCUMENTS

JP    2000197883 A  *  7/2000

*Primary Examiner* — Hirdepal Singh
(74) *Attorney, Agent, or Firm* — Snell & Wilmer LLP (57) ABSTRACT

A pool floatation device including a body configured to float on the surface of water of a pool. A sonar device may be coupled to the body and configured to detect movement of an object beneath the surface of the water of the pool. A wireless communication device may be coupled to the body and configured to transmit a wireless signal for indicating to a terminal device that the sonar device has detected movement of the object beneath the surface of the water of the pool.

15 Claims, 8 Drawing Sheets

(56) References Cited

U.S. PATENT DOCUMENTS

2016/0155314 A1\* 6/2016 Snyder ................. G08B 21/084
                                                               340/573.6
2017/0212532 A1\* 7/2017 Potucek ............... A61H 33/005

\* cited by examiner

POOL FLOATATION DEVICE WITH SONAR

CROSS-REFERENCE TO RELATED APPLICATIONS

This application claims the benefit of U.S. Provisional Application No. 62/236,015, filed Oct. 1, 2015, the entire contents of which are incorporated herein by reference.

BACKGROUND

Young children and other individuals who cannot swim or swim well, often play around the area surrounding a pool. If such an individual were to fall into the pool, the individual may drown unless another party were notified in enough time to prevent the drowning. In addition, pool water quality may be difficult or unmanageable for a user to frequently check and maintain. It may be desirable to produce an improved device, system, or method for enhancing pool safety and for maintaining pool water quality.

SUMMARY

In light of the aforementioned need in the art, the present disclosure includes a pool floatation device. The pool floatation device may include a body configured to float on the surface of water of a pool. A sonar device may be coupled to the body and configured to detect movement of an object beneath the surface of the water of the pool. A wireless communication device may be coupled to the body and configured to transmit a wireless signal for indicating to a terminal device that the sonar device has detected movement of the object beneath the surface of the water of the pool.

The present disclosure also includes a pool floatation device. The pool floatation device may include a body configured to float on the surface of water of a pool. A water quality detection device may be coupled to the body and configured to detect a water quality of the water of the pool. A wireless communication device may be coupled to the body and configured to transmit a wireless signal for indicating to a terminal device the water quality detected by the water quality detection device.

The present disclosure also includes a method. The method may include detecting, with a sonar device coupled to a body floating in a pool, movement of an object beneath the surface of water of the pool. The method may include transmitting, with a wireless communication device coupled to the body, a wireless signal for indicating to a terminal device that the sonar device has detected the movement of the object beneath the surface of the water of the pool.

The present disclosure also includes a method. The method may include receiving, with the mobile device, a wireless signal indicating that a sonar device in a pool has detected movement of an object beneath the surface of water of the pool. The method may include producing, with the mobile device, a notification that the sonar device in the pool has detected movement of the object beneath the surface of the water of the pool.

BRIEF DESCRIPTION OF THE DRAWINGS

Features and advantages of the systems, apparatuses, and methods as disclosed herein will become appreciated as the same become better understood with reference to the specification, claims, and appended drawings wherein:

DETAILED DESCRIPTION

Figure 1:
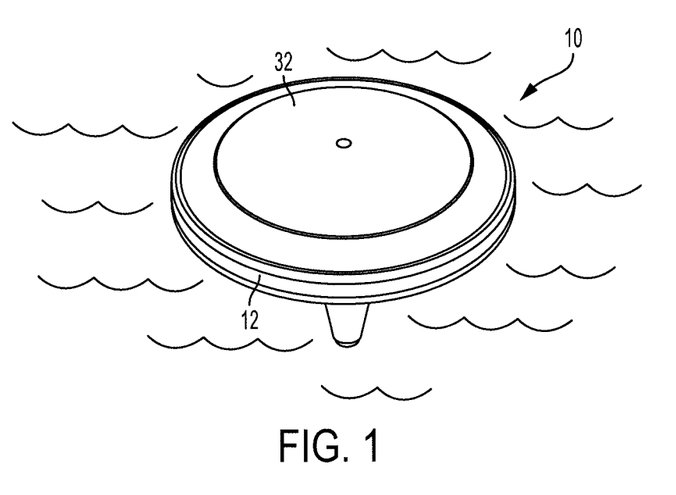
FIG. 1 illustrates a perspective view of a floatation device according to an embodiment of the present disclosure.

FIG. 1 illustrates a perspective view of a floatation device 10 according to an embodiment of the present disclosure. The floatation device 10 may include a body 12 configured to float in water of a pool. The pool may include a swimming pool, or spa or hot tub, or other form of pool. The body 12 may be free to float throughout the pool.

In one embodiment, the device 10 may be configured in a manner to be fixed or tethered to a portion of the pool. The portion of the pool may include a surface of the pool including a side wall or a bottom of the pool. The body 12 may be fixed or tethered to a surface outside of the pool.

Figure 2:
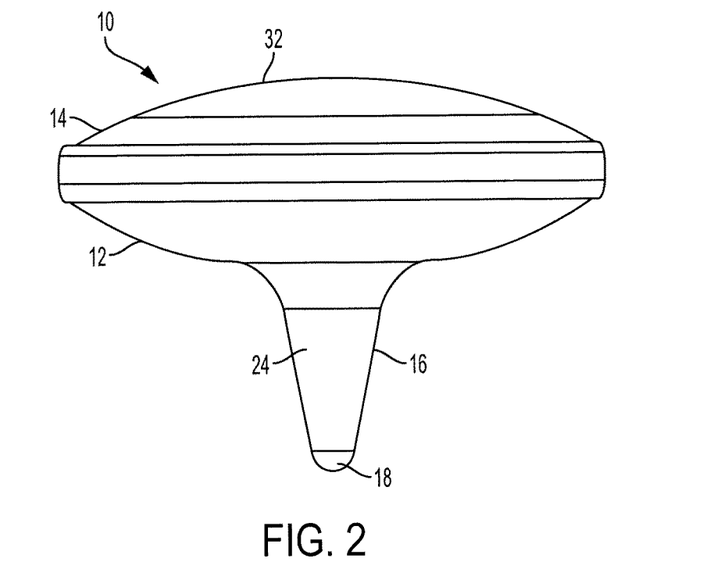
FIG. 2 illustrates a side view of a floatation device according to an embodiment of the present disclosure.

FIG. 2 illustrates a side view of the floatation device 10. The body 12 of the floatation device 10 may include an upper portion 14 and a lower portion 16. The upper portion 14 may have a disc shape. The lower portion 16 may protrude away from the upper portion 14, and may have a conical shape. The upper portion 14 may pass through or rest on the surface of the water of the pool. The lower portion 16 may be positioned in the water of the pool when the body floats on the surface of the water of the pool. In other embodiments, the shape of the body may differ from the shape shown in FIG. 2.

The body 12 may be hollow to create buoyancy or may be made of materials less dense than water to allow for floatation. In one embodiment, other methods to create floatation may be used.

In one embodiment, the body 12 may be configured to be positioned beneath the surface of the pool of water. For example, the body 12 may be configured to float in an intermediate position beneath the surface of the water, or may be positioned at the bottom of the pool.

A sonar device 18 may be coupled to the body 12. The sonar device 18 may be positioned on the lower portion 16.

The sonar device 18 may be configured to be positioned beneath the surface of the water of the pool during operation of the floatation device 10, to detect acoustic signals beneath the surface of the water of the pool. In one embodiment, the sonar device 18 may be positioned in a different location than shown in FIG. 2. For example, the sonar device 18 may be positioned on the upper portion 14, or may be configured to be positioned above the surface of the water to detect sounds beneath the surface of the water.

The sonar device 18 may include an acoustic transmitter and an acoustic receiver. In one embodiment, the sonar device 18 may include only an acoustic receiver. The sonar device 18 may be a passive sonar device, which detects acoustic signals from the water of the pool. The acoustic signals may be sounds beneath the surface of the water. The sonar device 18 may be configured to detect when an acoustic signal has a property greater than a threshold value. For example, the threshold value may be an amplitude or matching characteristic for a particular sound profile. The sonar device 18 may be configured to detect movement of an object beneath the surface of the water of the pool, which includes an object falling into the pool and accordingly making a sound beneath the surface of the pool.

The sonar device 18 may be configured as an active sonar device. The active sonar device may use an acoustic transmitter and an acoustic receiver. The sonar device 18 may be configured to transmit an acoustic signal via the acoustic transmitter. The acoustic signal may be reflected off the surfaces of the pool and return to the acoustic receiver of the sonar device 18. The sonar device 18 may detect the timing of the returned acoustic signal to determine the spatial configuration of the surfaces of the pool. If an object falls in the pool, the sonar device 18 may be configured to detect the change in the timing of the returned acoustic signal, and may be configured to detect movement of an object beneath the surface of the pool, including an object having fallen in the pool.

The sonar device 18 may be configured to detect a change in a property of the acoustic signal that is greater than a threshold to determine that an object has fallen into the pool. The property may be a timing of the returned signal. The threshold may allow the sonar device to distinguish between an object falling into the pool, and merely movement of the body 12 or sonar device 18, which may cause a different timing of the return signal.

In one embodiment, the sonar device 18 may be configured as an active sonar device that is configured to detect a property of the returned acoustic signal in the form of the frequency of the returned acoustic signal. The doppler shift may be caused by rapid movement of an object beneath the surface of the pool water. If an object falls in the pool, the sonar device 18 may be configured to detect the change in the frequency of the returned signal, and may be configured to detect an object has fallen into the pool. The sonar device may be configured to detect that the change in the frequency of the acoustic signal is greater than a threshold to determine that an object has fallen into the pool. The threshold may allow the sonar device 18 to distinguish between an object falling into the pool, and merely movement of the body 12 or sonar device 18, which may cause a different change in frequency of the return signal.

Figure 3:
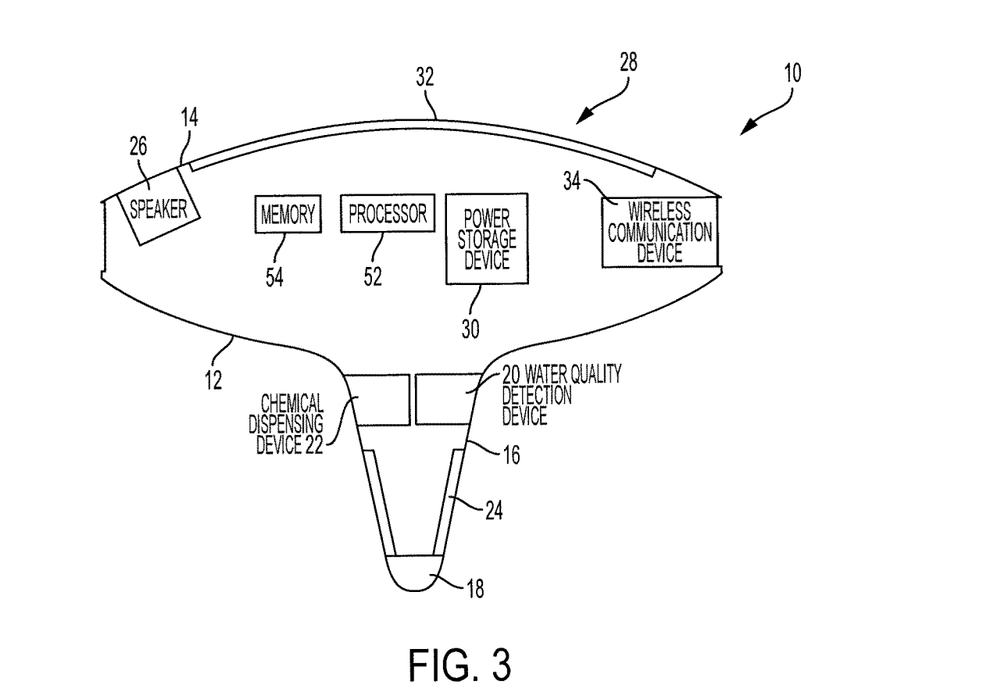
FIG. 3 illustrates a side cross sectional view of a floatation device according to an embodiment of the present disclosure.

FIG. 3 illustrates a side cross sectional view of the floatation device 10. The sonar device 18 may be positioned at a lowermost point of the body 12.

The floatation device 10 may include a water quality detection device 20. The water quality detection device 20 may be coupled to the body 12. The water quality detection device 20 may be configured to detect a quality of the water of the pool. The water quality detection device 20 may be configured to be positioned beneath the surface of the water to detect a water quality of the water. The water quality detection device 20 may be configured to be positioned on the lower portion 16 of the body 12. The water quality detection device 20 may be configured to detect any feature of quality of the water, which may include chemical factors of the water, chemical levels of the water, or contaminant levels of the water.

The chemical factors of the water may include such features as a pH level of the water, a total alkalinity level of the water, a calcium hardness of the water, or other chemical factors of the water. The water quality detection device 20 may be configured to detect a value corresponding to each or all of the chemical factors of the water.

The chemical levels of the water may include such features as a disinfectant level of the water, including a level of chlorine, bromine or other disinfectants of the water. The chemical levels of the water may include a metal level of the water, such metals including copper or iron, or other metals. Other chemical levels may be detected by the water quality detection device 20. The water quality detection device 20 may be configured to detect a value corresponding to each or all of the chemical levels of the water.

The contaminant levels of the water may include such features as contaminants such as bacteria, viruses, microorganisms such as algae and other microorganisms, chloramines, and other human introduced contaminants such as sweat, urine, feces, and body products such as sunscreen, suntan lotion, hair care products, makeup, and other body products. The water quality detection device 20 may be configured to detect a value corresponding to each or all of the contaminant levels of the water.

The floatation device 10 may include a chemical dispensing device 22. The chemical dispensing device 22 may be coupled to the body 12. The chemical dispensing device 22 may be configured to dispense a chemical into the water of the pool. The chemical dispensing device 22 may be configured to be positioned beneath the surface of the water to dispense a chemical into the water of the pool. The chemical dispensing device 22 may be configured to be positioned on the lower portion 16 of the body 12. In one embodiment, the device 22 may be configured to be positioned on the surface of the water to dispense the chemical into the water of the pool.

The chemical that is dispensed by the chemical dispensing device 22 may be configured to counteract any feature of quality of the water detected by the water quality detection device 20.

For example, the chemical dispensed by the chemical dispensing device 22 may be configured to counteract a chemical factor of the water. For example, if a pH level of the water is high, the chemical dispensing device may be configured to dispense an acid into the water. The acid may be hydrochloric acid or another form of acid. If a pH level of the water is too low, the chemical dispensing device 22 may be configured to dispense a base into the water. The base may be soda ash or another form of base. If the alkalinity level is high, the chemical dispensing device may be configured to dispense an acid into the water. If the alkalinity level is low, the chemical dispensing device 22 may be configured to dispense a base into the water. The base may be sodium bicarbonate or another form of base. If the calcium hardness level is high, the chemical dispensing device 22 may be configured to dispense a flocculant or another suitable chemical into the water. If the calcium hardness level is low, the chemical dispensing device 22 may be configured to dispense calcium chloride or another suitable chemical into the water.

The chemical dispensed by the chemical dispensing device 22 may be configured to counteract a chemical level of the water. For example, if a disinfectant level of the water is low, the chemical dispensing device 22 may be configured to dispense disinfectant into the water. The disinfectant may include chlorine or bromine, or another suitable disinfectant.

The chemical dispensed by the chemical dispensing device 22 may be configured to counteract a contaminant level of the water. For example, if a contaminant level of the water is high, the chemical dispensing device 22 may be configured to dispense disinfectant into the water. The disinfectant may include chlorine or bromine, or another suitable disinfectant. If a chloramine level of the water is high, the chemical dispensing device may be configured to dispense a chlorine shock treatment to the water.

The chemical dispensing device 22 may include a receptacle for storing any of the chemicals dispensed by the device 22. Multiple receptacles may be used to store and separate different chemicals used by the device 22.

The floatation device 10 may include a light 24. The light 24 may be configured to illuminate such that light is visible from outside of the body 12. The light 24 may be configured to be positioned on the lower portion 16 of the body 12. As shown in FIGS. 2 and 3, the light 24 may extend around the lower portion 16 of the body 12, and may have a conical outer surface to match the shape of the outer surface of the lower portion 16 of the body 12. The light 24 may be positioned to illuminate beneath the surface of the water when the floatation device 10 is in use. In one embodiment, the light 24 may be positioned on the upper portion 14 of the body 12 or on another portion of the body 12. In one embodiment, the light 24 may be configured to illuminate above the surface of the water.

The floatation device 10 may include a speaker 26. The speaker 26 may be coupled to the body 12. The speaker 26 may be configured to emit a sound audible from outside the body 12.

The floatation device 10 may include a power source 28. The power source 28 may be coupled to the body 12. The power source 28 may include a power storage device 30, which may include a battery such as a rechargeable or non-rechargeable battery. In one embodiment, the power storage device 30 may include a capacitor or supercapacitor. In one embodiment, the power source 28 may include a solar panel 32 for charging the power storage device 30. The solar panel 32 may be positioned at the top surface of the upper portion 14, for receiving incident sunlight during use of the floatation device 10. The power source 28 may be configured to deliver power to the components of the floatation device 10.

Figure 4:
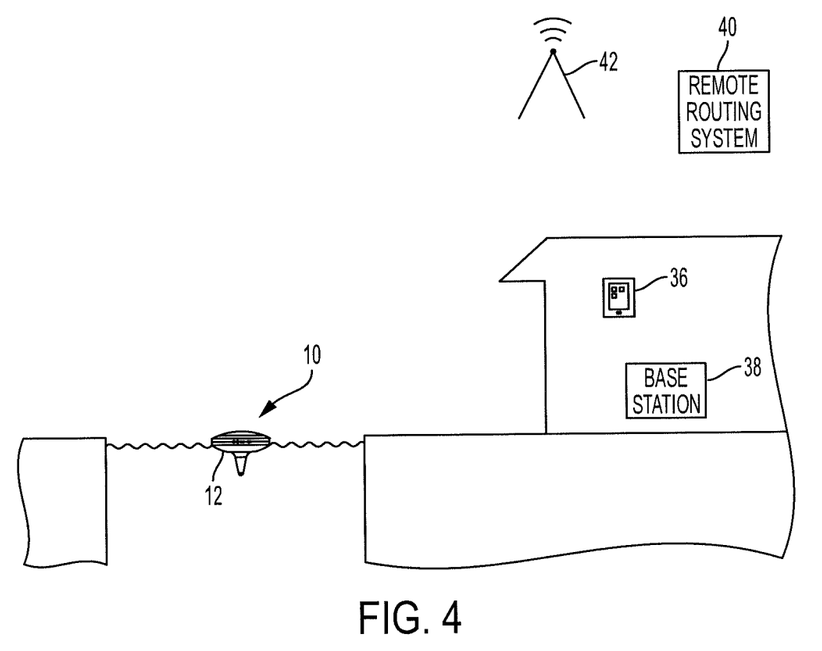
FIG. 4 illustrates a schematic of the operation of a wireless communication device according to an embodiment of the present disclosure.

The floatation device 10 may include a wireless communication device 34. The wireless communication device 34 may be coupled to the body 12. The wireless communication device 34 may include a transmitter and a receiver configured to transmit or receive a wireless signal, respectively, from the body 12. The wireless communication device 34 may be configured to operate according to a variety of protocols and other means, for example, the wireless communication device 34 may be configured to operate via a radio transmission, a wifi transmission, a Bluetooth transmission, a cellular transmission, a peer-to-peer transmission, a satellite transmission, and/or another form of wireless transmission. Referring to FIG. 4, the wireless communication device 34 may be configured to transmit and/or receive a wireless signal to or from a terminal device 36. The wireless communication device 34 may be configured to directly communicate with the terminal device 36. In one embodiment, the wireless communication device 34 may be configured to use an intermediate transmission device to communicate with the terminal device 36, depending on the type of wireless communication used. For example, in a wifi transmission system, a local base station 38 may be used to communicate with the wireless communication device 34 and the terminal device 36. The base station 38 may be in the form of a local wifi modem or router used to communicate with the terminal device 36. In one embodiment, the base station 38 may be configured to communicate with an intermediate transmission device in the form of a remote routing system 40 to communicate with the terminal device 36. In one embodiment, the remote routing system 40 may be a cloud remote routing system to communicate with the terminal device 36. As an additional example, in a cellular transmission system, the wireless communication device 34 may communicate with an intermediate transmission device in the form of a cellular tower 42 or the like. One or more intermediate transmission devices may be utilized with any of the forms of wireless communication used by the wireless communication device 34.

The wireless communication device 34 may be configured to transmit or receive a wireless signal, which may be in the form of a telephone signal, an email signal, a text message signal, a fax signal, a data signal, and/or another form of wireless signal.

Figure 5:
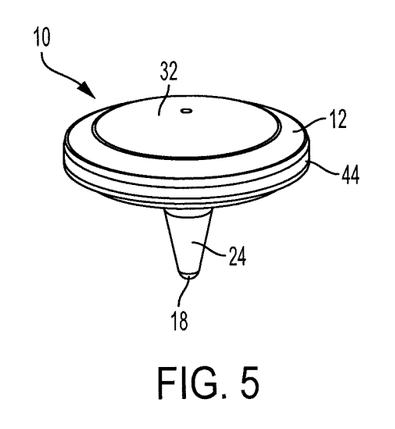
FIG. 5 illustrates a perspective view of a floatation device according to an embodiment of the present disclosure.

Referring to FIG. 5, the body 12 of the floatation device 10 may include a ring 44. The ring 44 may be configured to extend around the outer circumference of the remaining portion of the body 12. The ring 44 may be configured to be removable from the remaining portion of the body 12. The ring 44 may be configured to conceal controls of the floatation device 10 and form a seal to prevent water from contacting the controls. The ring 44 may be positioned in a channel 46 extending around the outer circumference of the remaining portion of the body 12. The ring 44 may be configured to enhance the buoyancy of the floatation device 10 by being made of a buoyant material such as rubber or other buoyant materials.

Figure 6:
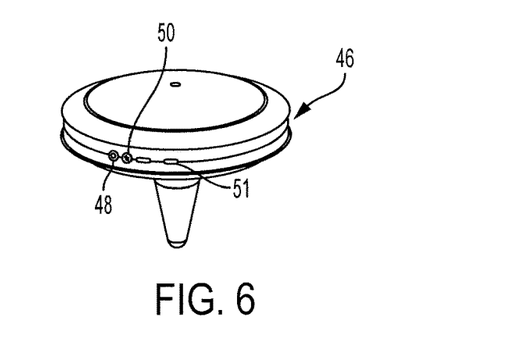
FIG. 6 shows a perspective view of a floatation device with a ring removed, according to an embodiment of the present disclosure.

FIG. 6 shows a perspective view of the body 12 of the floatation device 10 with the ring 44 removed. Controls of the floatation device 10 are positioned in the channel 46. The controls may include a power switch 48 for turning the power of the floatation device 10 on or off. The controls may include a light switch 50 for turning the light 24 on or off. The controls may include data ports 51 for allowing an update of the firmware of the components of the floatation device, or for other control or communication with components of the floatation device 10.

Referring to FIG. 3, the floatation device 10 may include a processor 52 and a memory 54. The processor 52 and memory 54 may each be coupled to the body 12. The processor may be configured to operate the functions of the floatation device. The memory 54 may be configured to store data or other information for use by the processor 52 or other components of the floatation device 10.

The processor 52 may be configured to operate the functions of the sonar device 18. The processor 52 may be configured to determine when the sonar device 18 detects movement of an object beneath the surface of the water of the pool. The processor 52 may be configured to determine when an acoustic signal detected by the sonar device 18 has a property that is greater than a threshold value. For example, the processor 52 may determine that the acoustic signal has an amplitude greater than a value, or the acoustic signal matches a sound profile, or a timing or frequency of the acoustic signal is greater than a value, or another property of the acoustic signal is greater than a value. The processor 52 may be configured to determine that movement of an object beneath the surface of the water of the pool has occurred, which includes a determination that an object has fallen into the water of the pool. The threshold value may be stored in the memory 54, and may be updated upon the wireless communication device 34 receiving a wireless signal indicating the threshold value, or another input to the floatation device 10 receiving an indication of the threshold value.

The processor 52, in response to a determination that the sonar device 18 has detected movement of an object beneath the surface of the water of the pool, may cause the wireless communication device 34 to transmit a wireless signal. The wireless signal may indicate to a terminal device that the sonar device 18 has detected movement of the object beneath the surface of the water of the pool. The processor 52, in response to a determination that the sonar device 18 has detected movement of an object beneath the surface of the water of the pool, may cause the light 24 to illuminate and/or the speaker 26 to produce sound. The illumination of the light 24 and the sound produced by the speaker 26 may serve as an alarm, for example, to indicate that an object has fallen into the water of the pool. If the object is a child, for example, a nearby individual may be able to rescue the child from drowning in the pool. The processor 52 may be configured to turn on or off the sonar device 18 or turn on or off the light 24 or speaker 26.

The processor 52 may be configured to operate the functions of the water quality detection device 20. The processor 52 may be configured to determine when the water quality detected by the water quality detection device 20 is greater than or less than a threshold value. The determination may include a determination as to any feature of quality of the water, which may include chemical factors, chemical levels, or contaminant levels of the water. The threshold value may be stored in the memory 54, and may be updated upon the wireless communication device 34 receiving a wireless signal indicating the threshold value, or another input to the floatation device 10 receiving an indication of the threshold value.

The processor 52, in response to a determination of the water quality, may cause the wireless communication device 34 to transmit a wireless signal. The wireless signal may indicate to a terminal device 36 the water quality detected by the water quality detection device 20. The wireless signal may indicate a measure of the water quality detected by the water quality detection device 20. For example, the wireless signal may indicate a level of the amount of chlorine in the pool, or the pH level of the water of the pool. The wireless signal may indicate any feature of the water quality detected by the water quality detection device 20. The processor 52, in response to a determination of the water quality, may cause the light 24 to illuminate and/or the speaker 26 to produce sound. The illumination of the light 24 and the sound produced by the speaker 26 may serve as an alarm, for example, to indicate the water quality level of the water in the pool. For example, if a pH level or a contaminant level of the water of the pool is unsatisfactory for an individual to swim in, then the alarm may indicate to the individual to not enter the pool. The processor 52 may be configured to turn on or off the water quality detection device 20 or turn on or off the light 24 or speaker 26.

The processor 52 may be configured to operate the functions of the chemical dispensing device 22. The processor 52 may be configured to cause the chemical dispensing device 22 to dispense one or more chemicals in the water of the pool. The processor 52 may be configured to automatically cause a chemical to be dispensed into the pool. The processor 52 may be configured to automatically dispense the chemical into the pool in response to a determination of the water quality detected by the water quality detection device 20. For example, if the pH level of the water is detected to be below a desired threshold value, the processor 52 may be configured to automatically dispense a chemical into the water of the pool to increase the pH level of the water. The processor 52 may be configured to automatically dispense the chemical into the pool in response to a set schedule, which may be stored in the memory 54. For example, the processor 52 may be configured to automatically dispense a chemical such as chlorine into the pool at a set time or date. The schedule may be stored in the memory 54, and may be updated upon the wireless communication device 34 receiving a wireless signal indicating the schedule, or another input to the floatation device 10 of the schedule.

The wireless communication device 34 may be configured to receive a signal, for example, from the terminal device 36, which may cause the processor 52 to dispense the chemical from the chemical dispensing device 22. Another form of input may be provided to the floatation device 10 to cause the floatation device to dispense the chemical into the water of the pool. In one embodiment, the wireless communication device 34 may be configured to receive a signal to update the firmware of the components.

The processor 52 may be configured to cause the wireless communication device 34 to transmit a wireless signal. The wireless signal may indicate to a terminal device that the chemical dispensing device 22 has dispensed a chemical into the water of the pool. The processor 52 may be configured to determine an amount of one or more chemical remaining in a receptacle of the chemical dispensing device 22. The processor 52 may be configured to cause the wireless communication device 34 to transmit a wireless signal, for example, to the terminal device 36, which indicates the amount of chemical remaining in the chemical dispensing device 22. An individual may be notified to refill the chemicals in the chemical dispensing device 22 in response to receiving the signal.

The processor 52 may be configured to operate the functions of the light 24 and the speaker 26. The processor 52 may be configured to automatically cause the light 24 or the speaker 26 to be activated. For example, the processor 52 may be configured to cause the light 24 or speaker 26 to be activated to serve as an alarm in response to the operation of the sonar device 18 or the water quality detection device 20 or another component of the floatation device 10. The processor 52 may be configured to automatically cause the light 24 or the speaker 26 to be activated in response to a set schedule, which may be stored in the memory 54. For example, the processor 52 may be configured to automatically activate the light 24 or speaker 26 at a set time or date. For example, the light 24 may be set to illuminate at night times. The schedule may be stored in the memory 54, and may be updated upon the wireless communication device 34 receiving a wireless signal indicating the schedule, or another input to the floatation device 10 of the schedule.

The wireless communication device 34 may be configured to receive a signal, for example, from the terminal device 36, which may cause the processor 52 to activate the light 24 or speaker 26. Another form of input may be provided to the floatation device 10 to cause the processor 52 to activate the light 24 or speaker 26.

The processor 52 may be configured to control operation of the power source 28. The processor 52 may be configured to cause the wireless communication device 34 to send a signal, for example, to the terminal device 36, to wirelessly indicate a power level of the power source 28. In one embodiment, the processor 52 may be configured to cause the light 24 or the speaker 26 to activate in response to a power level of the power source 28. For example, the light 24 or speaker 26 may activate to serve as an alarm indicating a low power level of the power source 28. The processor 52 may be configured to control operation of the wireless communication device 34. The processor 52 may be configured to allow the wireless communication device 34 to receive or transmit any wireless signal from the body 12.

Figure 7:
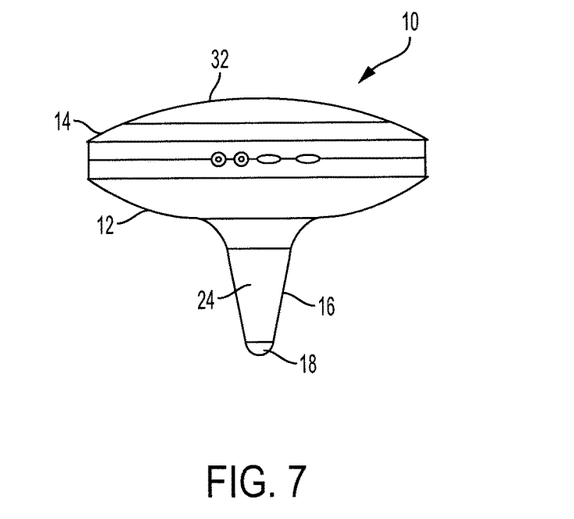
FIG. 7 illustrates a side view of the floatation device with a ring removed, according to an embodiment of the present disclosure.
Figure 8:
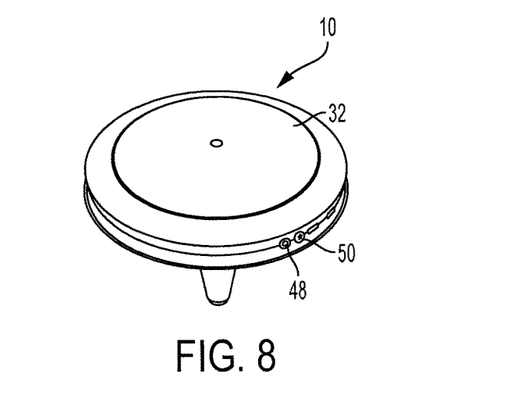
FIG. 8 shows a perspective view of a floatation device with a ring removed, according to an embodiment of the present disclosure.
Figure 9:
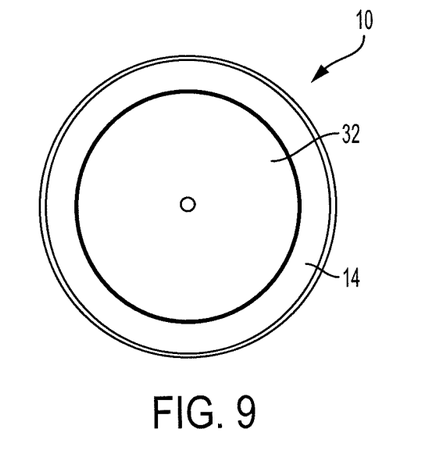
FIG. 9 illustrates a top view of a floatation device according to an embodiment of the present disclosure.
Figure 10:
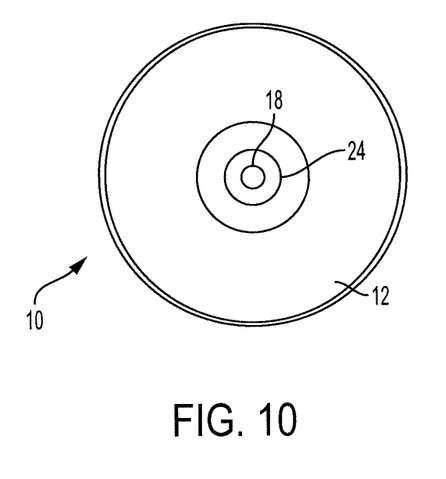
FIG. 10 illustrates a bottom view of a floatation device according to an embodiment of the present disclosure.

FIG. 7 illustrates a side view of the floatation device 10 with the ring 44 separated from the remainder of the body. FIG. 8 illustrates a side perspective view of the floatation device 10 with the ring 44 separated from the remainder of the body. FIG. 9 illustrates a top view of the floatation device 10. FIG. 10 illustrates a bottom view of the floatation device 10.

Referring back to FIG. 4, the wireless communication device 34 of the floatation device 10 may communicate wirelessly with the terminal device 36. The terminal device may be a device for receiving and/or sending wireless signals from or to the floatation device 10, respectively. The terminal device 36 may be a communications device such as a telephone, fax machine or the like, or may be a computing device such as a desktop, or laptop computer, or a mobile device such as a tablet computer or a programmable cellular phone or smartphone. In one embodiment, the terminal device 36 may be a dedicated device that may be specifically for use with the floatation device 10. In one embodiment, the terminal device 36 may be another form of terminal device.

The terminal device 36 may operate using the components equipped with the terminal device 36. For example, if the terminal device 36 is a telephone, the terminal device may operate using the call receiver of the terminal device 36. If the terminal device 36 is a mobile device, the terminal device may operate using the call receiver of the terminal device 36. In one embodiment, the terminal device 36 may operate using software, which may be installed, for use with the floatation device 10. For example, a mobile device may utilize an application or "app" or other software that is installed on the mobile device for use for communication with the floatation device 10.

The terminal device 36 may be configured to produce a notification in response to a signal received from the floatation device 10. The notification may be a sound, a movement, an indicator produced on a display or other component of the terminal device 36, or other form of notification. For example, the notification could be a ringtone, a vibration, or an electronic notification produced on the screen of a desktop computer or mobile device. In one embodiment, an application installed on the terminal device 36 may be configured to produce a notification on the terminal device 36.

The terminal device 36 may be configured to receive a wireless signal indicating that the sonar device 18 has detected movement of an object beneath the surface of the water of the pool. The movement may be an individual, such as a child, falling into the water of the pool, and accordingly, the wireless signal may serve as an alert regarding a child falling into the water of the pool. In response to the terminal device 36 receiving the wireless signal, the terminal device 36 may produce a notification that the sonar device 18 has detected movement of the object beneath the surface of the water of the pool. Multiple notifications may be provided by the terminal device 36, for example, flashing lights, sound, movement, and indicators on a display screen may be produced. The multiple notifications may correspond to the multiple forms in which the wireless signal may be transmitted to the terminal device 36. For example, a ringtone may be produced in response to a telephone signal being sent, a text message indicator may be produced in response to a text message being sent, an email indicator may be produced in response to an email message being sent, a wall alarm device may produce a sound in response to the wireless signal, among other notifications. Multiple terminal devices 36 may produce a notification. For example, a mobile device, a desktop computer, a telephone, and a dedicated wall device or the like may each produce a notification to assure that an individual is alerted that a child has fallen into the water of the pool through various means.

An application installed on the terminal device 36 may be configured to produce a notification regarding the detection of movement of an object beneath the surface of the water of the pool. The notification may be configured to override any other application or other system running on the terminal device 36 to produce the notification. For example, if a user is using a mobile device as a cellular phone, the application may be configured to override the phone processes of the mobile device to produce a sound or other notification regarding the movement of the object beneath the surface of the water of the pool.

The terminal device 36 may be configured to receive a wireless signal indicating a water quality detected by the water quality detection device 20. In response to the terminal device 36 receiving the wireless signal, the terminal device 36 may produce a notification of the water quality detected by the water quality detection device 20. Multiple notifications and multiple terminal devices 36 may produce notifications in a similar manner as the notification indicating movement of an object beneath the surface of the water. For example, a notification may be provided on a terminal device 36 that the water in the pool is undesirable for use. In one embodiment, the notification may be a chart that is displayed on the display of the terminal device 36. The chart may display any level of water quality detected by the water quality detection device 20. For example, a chart may display a chemical factor of the water, a chemical level of the water, or a contaminant level of the water. The chart may allow a user to readily ascertain the water quality level detected by the water quality detection device 20. An application installed on the terminal device 36 may produce the chart of the water quality level. For example, a user may open an application on the terminal device 36 to readily determine the water quality level of the pool.

The terminal device 36 may be configured to receive a wireless signal indicating the operation of the dispensing device 22. In response to the terminal device 36 receiving the wireless signal, the terminal device 36 may produce a notification of the operation of the dispensing device 22. Multiple notifications and multiple terminal devices 36 may produce notifications in a similar manner as the notification indicating movement of an object beneath the surface of the water. For example, a notification may be provided on a terminal device 36 that the dispensing device 22 has dispensed a chemical, or that a chemical level in a receptacle of the dispensing device 22 is low. An application installed on the terminal device 36 may produce the notification of the operation of the dispensing device 22. For example, a user may open an application on the terminal device 36 to readily determine whether the dispensing device 22 has dispensed chemicals, or a level of chemicals in the dispensing device 22.

The terminal device 36 may be configured to receive a wireless signal indicating the operation of the light 24, the speaker 26, and/or the power source 28. In response to the terminal device 36 receiving the wireless signal, the terminal device 36 may produce a notification of the operation of the corresponding light 24, speaker 26, or power source 28. Multiple notifications and multiple terminal devices 36 may produce notifications in a similar manner as the notification indicating movement of an object beneath the surface of the water. For example, a notification may be provided on a terminal device 36 that the light or speaker is on or off, or the power source is charging or low on power. An application installed on the terminal device 36 may produce the notification of the operation of the dispensing device 22. For example, a user may open an application on the terminal device 36 to readily determine the operation of the light 24, speaker 26, or power source 28.

The terminal device 36 may be configured to transmit information to the wireless communication device 34. The terminal device 36 may communicate with the floatation device 10 using the components equipped with the terminal device 36 or may be programmed with an application or other software that allows the user to control operation of the floatation device 10. The application or other software may include a graphical user interface or other input means that allow a user to control operation of the floatation device. The terminal device 36 may be used to control operation of the sonar device 18, which may include setting a mode of operation of the sonar device 18 or a threshold value for the sonar device 18. The mode of operation may be to turn on or off the sonar device 18, or to switch between active or passive sonar or another mode of operation. The terminal device 36 may be used to set a time schedule for the time that the sonar device 18 operates.

The terminal device 36 may be used to control operation of the water quality detection device 36. The terminal device 36 may set a threshold for water quality. The terminal device 36 may also set which types of water quality that the water quality detection device 36 detects.

The terminal device 36 may be used to control operation of the dispensing device 22. The terminal device may be used to set a schedule of dispensing any of the chemicals of the chemical dispensing device 22. In one embodiment, the terminal device 36 may be configured to send a signal to the dispensing device 22 causing the dispensing device 22 to dispense a chemical.

The terminal device 36 may be used to control operation of the light 24. The terminal device 36 may be used to set a schedule for the light 24 to be illuminated. In one embodiment, the terminal device 36 may be configured to send a wireless signal to the light 24 causing the light 24 to turn on or off.

The terminal device 36 may be used to control operation of the speaker 26. The terminal device 36 may be used to set a schedule of the speaker 26 emitting sound. In one embodiment, the terminal device may be configured to send a signal to the speaker 26 causing the speaker to emit or not emit sound.

Figure 11:
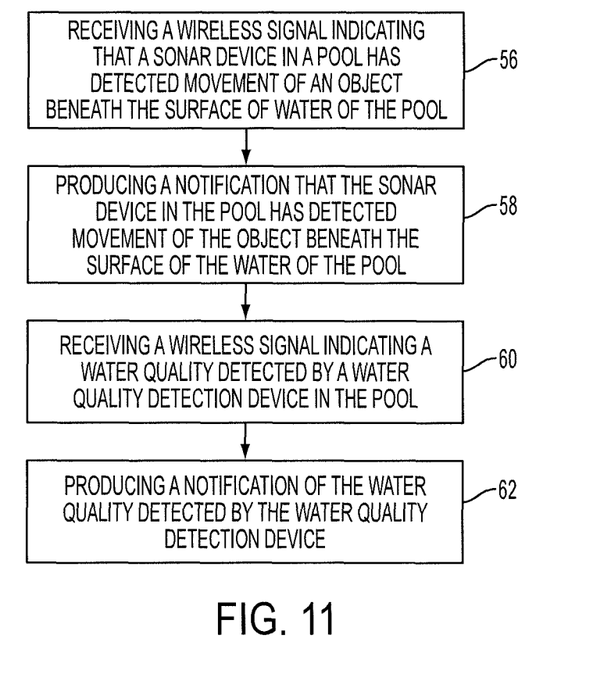
FIG. 11 illustrates a method which may be performed by a terminal device according to an embodiment of the present disclosure.

FIG. 11 illustrates a method which may be performed by the terminal device 36. The method may be performed by software of the terminal device 36. The method may also be performed by a processor configured to perform the steps of the method. In an embodiment in which the terminal device 36 is a mobile device, the method may be performed by software loaded on the mobile device. The method may include a step 56 of receiving a wireless signal indicating that the sonar device 18 in a pool has detected movement of an object beneath the surface of water of the pool. The movement may indicate that an individual, such as a child, has fallen into the pool. The method may include a step 58 of producing a notification that the sonar device 18 in the pool has detected movement of the object beneath the surface of the water of the pool. The notification may be selected from a group consisting of a sound, a movement, and indicator displayed on the screen of the terminal device, and combinations thereof.

The method may include a step 60 of receiving a wireless signal indicating a water quality detected by the water quality detection device 20 in the pool. The water quality may any form of water quality that is detected by the water quality detection device 20. The method may include a step 62 of producing a notification of the water quality detected by the water quality detection device 20. The notification may be an indicator displayed on a screen of the terminal device 36. The indicator may be a chart. The chart may display the levels of water quality detected by the water quality detection device 20.

The method of FIG. 11 may be varied or modified to perform any of the processes disclosed herein regarding the terminal device 36.

Figure 12:
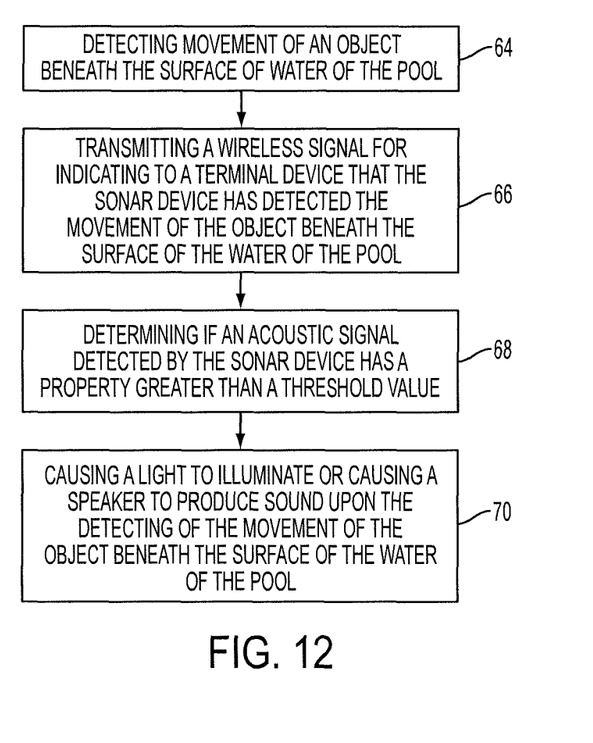
FIG. 12 illustrates a method which may be performed by a floatation device according to an embodiment of the present disclosure.
Figure 13A:
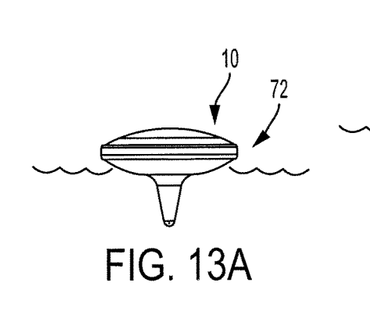
FIGS. 13A-13D illustrate a method according to an embodiment of the present disclosure.
Figure 13B:
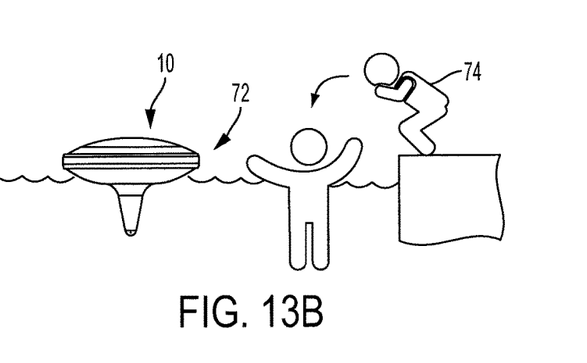
Figure 13C:
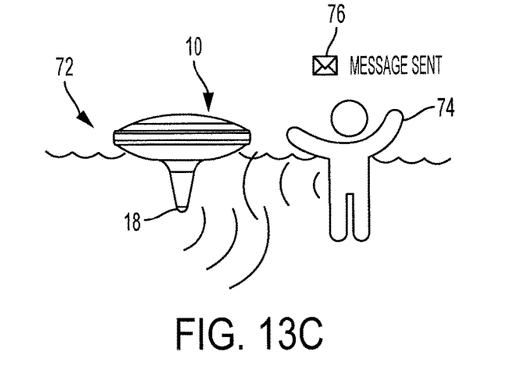
Figure 13D:
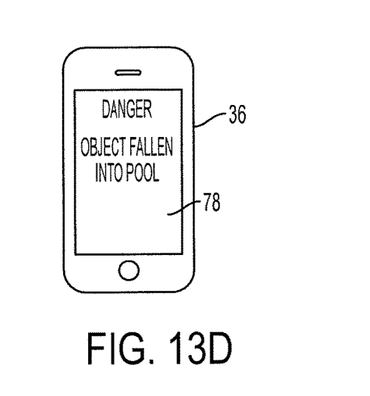

FIG. 12 illustrates a method which may be performed by the floatation device 10. The method may be performed by components of the floatation device 10. Steps of the method may also be performed by the processor 52, which may be configured to perform the steps of the method, or may be programmed with software for performing the steps of the method. The method may include a step 64 of detecting movement of an object beneath the surface of water of the pool. The step 64 may be performed by the sonar device 18. The movement of the object may indicate that an individual, such as a child, has fallen into the water of the pool. The method may include a step 66 of transmitting a wireless signal for indicating to the terminal device 36 that the movement of the object has been detected. The wireless signal may indicate that the sonar device 18 has detected the movement of the object. The step 66 of transmitting may be performed by the wireless communication device 34.

The method may include a step 68 of determining if an acoustic signal detected by the sonar device 18 has a property greater than a threshold value. The step 68 may be performed by the processor 52. The method may include a step 70 of causing the light 24 to illuminate or causing a speaker 26 to produce sound upon the detecting of the movement of the object beneath the surface of the water of the pool. The step 70 may be performed by the processor 52.

The method of FIG. 12 may be varied or modified to perform any of the processes disclosed herein regarding the floatation device 10. For example, the method may include detecting, with the water quality detection device 20, a water quality of the water of the pool. The method may include dispensing, with the chemical dispensing device 22, a chemical into the water of the pool. Other processes disclosed herein may be performed.

In operation, the floatation device 10 may be configured to provide an alert if an individual, such as a child, or other object falls in the pool. The floatation device 10 may be configured to provide an alert via lights, sound, or a wireless signal transmitted to a terminal device, or any combination thereof. The alert may take the form of a notification of the terminal device 36. A user may be capable of using the terminal device 36 to turn off the alert.

FIG. 13, for example, illustrates a method of alerting regarding the presence of an object beneath the surface of the water of a pool 72. In FIG. 13A, the floatation device 10 is floating on water of a pool 72. In FIG. 13B, a child 74 has fallen into the water of the pool 72. In FIG. 13C, the sonar device 18 detects the child 74 having fallen into the pool 72. The wireless communication device 34 sends a wireless signal 76 to the terminal device 36 indicating that the sonar device 18 has detected movement of an object beneath the surface of the water of the pool. In FIG. 13D, the terminal device 36 produces a notification 78 on the screen of the terminal device 36 that the sonar device 18 has detected movement of the object beneath the surface of the water of the pool.

The floatation device 10 may also be configured to provide an indication of the pool water quality. The indication of the pool water quality may be transmitted to a terminal device 36. For example, if the pH level of the pool water is at an undesired level, that information may be provided to the terminal device 36. The indication of the pool water quality may also result in an alert being emitted by the pool floatation device 10 in the form of a light notification or a speaker sound.

The floatation device 10 may also be configured to dispense a chemical into the pool water. The chemical may be dispensed automatically in response to a pool quality level being below a desired value, or may be dispensed in response to an input received by a user.

In one embodiment, the floatation device 10 may be used for illumination. The light 24 may be set to illuminate automatically at night or according to another schedule. The color of the light emitted by the light 24 may vary or rotate to provide an entertaining appearance for a party or the like. In one embodiment, the floatation device 10 may be used as a sound system. The speaker 26 may be configured to play sounds such as music or other sounds. The sounds emitted by the speaker 26 may be used for entertainment purposes such as at a party or the like.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary. The terms "approximate[ly]" and "substantial[ly]" represent an amount that may vary from the stated amount, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods.

These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A pool floatation device comprising:
    a body having an outer perimeter, and being configured to float on a surface of water of a pool, the body including an upper portion configured to be located above the surface of the water, and a lower portion protruding away from the upper portion and configured to be located below the surface of the water;

a set of device controls located along the outer perimeter of the body, between the upper portion of the body and the lower portion of the body, the set of device controls including at least a power switch and a data port for connecting a computing device;

a ring removably coupled to the body and located on top of the set of device controls, the ring configured to conceal the set of device controls and form a seal to prevent the water from contacting the set of device controls;

a sonar device coupled to the body and configured to use passive sonar to detect an object beneath the surface of the water of the pool by detecting an acoustic signal beneath the surface of the water and corresponding to a sound made by the object;

a memory positioned within the body and configured to store a plurality of sound profiles;

a processor connected to the memory and the sonar device, and configured to determine when the detected acoustic signal matches at least one sound profile of the plurality of sound profiles; and a wireless communication device coupled to the body, connected to the processor, and configured to transmit a wireless signal for indicating to a terminal device that the sonar device has detected the object beneath the surface of the water of the pool.

2. The pool floatation device of claim 1, wherein the sonar device is further configured to detect the object with active sonar.

3. The pool floatation device of claim 1, further comprising a light and a speaker, and wherein the processor is configured to:

cause the light to illuminate or the speaker to produce sound upon determining the detected acoustic signal matches the particular sound profile.

4. The pool floatation device of claim 3, wherein the wireless communication device is configured to receive a wireless signal indicating the particular sound profile.

5. A pool floatation device comprising:

a body configured to float on a surface of water of a pool, the body including an upper portion configured to be located above the surface of the water of the pool, and a lower portion protruding away from the upper portion and configured to be located inside the water;

a water quality detection device coupled to the lower portion of the body and configured to detect a water quality of the water of the pool;

a chemical dispensing device coupled to the lower portion of the body and configured to store a chemical and dispense the chemical into the water;

a wireless communication device coupled to the body and configured to:

transmit a wireless signal for indicating to a terminal device the water quality detected by the water quality detection device, and receive, from the terminal device, an indication by a user to dispense the chemical stored by the chemical dispensing device; and a processor coupled to the body, connected to the wireless communication device and the chemical dispensing device, and configured to immediately dispense the chemical upon receiving the indication to dispense the chemical is received from the terminal device.

6. The pool floatation device of claim 5, wherein the water quality detection device is configured to detect the water quality selected from a group consisting of chemical factors of the water, chemical levels of the water, contaminant levels of the water, and combinations thereof.

7. The pool floatation device of claim 5, wherein the wireless signal indicates a measure of the water quality detected by the water quality detection device.

8. The pool floatation device of claim 5, wherein the processor is further configured to:

determine when the water quality detected by the water quality detection device is greater than or less than a threshold value.

9. The pool floatation device of claim 8, further comprising a memory configured to store the threshold value, and wherein the wireless communication device is configured to receive a wireless signal indicating the threshold value.

10. The pool floatation device of claim 8, wherein the processor is configured to cause the chemical dispensing device to automatically dispense the chemical in response to the water quality being greater than or less than the threshold value.

11. A method comprising:

detecting, with a sonar device coupled to a body floating in a pool, using passive sonar, an acoustic signal beneath a surface of water of the pool and corresponding to a sound made by an object beneath the surface of the water of the pool;

storing, in a memory, a plurality of sound profiles;

determining, by a processor connected to the sonar device, when the detected acoustic signal matches at least one sound profile of the plurality of stored sound profiles;

providing an alert upon the detecting of the object beneath the surface of the water of the pool, the alert being illumination of a light located on the body or transmission of sound from a speaker located on the body;

transmitting, with a wireless communication device coupled to the body, a wireless signal for indicating to a terminal device that the sonar device has detected the object beneath the surface of the water of the pool;

producing, by the terminal device, a notification to a user that the sonar device has detected the object beneath the surface of the water of the pool;

receiving, by the terminal device from the user, an indication to disable the alert provided by the body floating in the pool; and disabling, by the terminal device via the wireless communication device, the alert provided by the body floating in the pool.

12. The method of claim 11, further comprising detecting, with a water quality detection device coupled to the body, a water quality of the water of the pool.

13. The method of claim 11, further comprising dispensing, with a chemical dispensing device coupled to the body, a chemical into the water of the pool.

14. A method comprising:

detecting, by a water quality detection device of a pool flotation device, a water quality of water in a pool;

determining, by a processor of the pool flotation device, that the water quality is below a threshold value;

communicating, by a wireless communication device of the pool flotation device to a mobile device, a signal indicating that the water quality is below the threshold value;

receiving, by the mobile device, the wireless signal indicating that the water quality is below the threshold value;

producing, by the mobile device, a notification associated with the detected water quality;

receiving, by the mobile device, an indication from a user to dispense a chemical from a chemical dispensing device of the pool flotation device;

communicating, by the mobile device to the wireless communication device of the pool flotation device, an indication to dispense the chemical; and immediately dispensing upon receiving the indication from the user, by the chemical dispensing device of the pool flotation device, the chemical into the water of the pool.

15. The method of claim 14, wherein the notification is selected from a group consisting of a sound, a movement, an indicator displayed on a screen of the mobile device, and combinations thereof.

* * * * *